(12) United States Patent
Kobayashi et al.

(10) Patent No.: US 12,240,794 B2
(45) Date of Patent: Mar. 4, 2025

(54) COMPOSITION FOR PRODUCING N-VINYL CARBOXYLIC ACID AMIDE

(71) Applicant: SHOWA DENKO K.K., Tokyo (JP)

(72) Inventors: Takamitsu Kobayashi, Fujisawa (JP); Naoyuki Tanaka, Kawasaki (JP)

(73) Assignee: Resonac Corporation, Tokyo (JP)

( * ) Notice: Subject to any disclaimer, the term of this patent is extended or adjusted under 35 U.S.C. 154(b) by 806 days.

(21) Appl. No.: 17/417,599

(22) PCT Filed: Dec. 23, 2019

(86) PCT No.: PCT/JP2019/050311
§ 371 (c)(1),
(2) Date: Jun. 23, 2021

(87) PCT Pub. No.: WO2020/137951
PCT Pub. Date: Jul. 2, 2020

(65) Prior Publication Data
US 2022/0112155 A1 Apr. 14, 2022

(30) Foreign Application Priority Data
Dec. 27, 2018 (JP) .................................. 2018-246081

(51) Int. Cl.
*C07C 231/12* (2006.01)
(52) U.S. Cl.
CPC .................................. *C07C 231/12* (2013.01)
(58) Field of Classification Search
None
See application file for complete search history.

(56) References Cited

FOREIGN PATENT DOCUMENTS

| JP | 2002-167369 A | 6/2002 |
| WO | 2010/079774 A1 | 7/2010 |
| WO | 2017/145569 A1 | 8/2017 |

OTHER PUBLICATIONS

Machine translation of Saihata (JP2002167369A, published on Jun. 11, 2002). (Year: 2002).*
Stackman ("Synthesis of N-Vinylacetamide and Preparation of Some Polymers and Copolymers" J. Am. Chem. Soc. 1985, p. 242) (Year: 1985).*
International Search Report of PCT/JP2019/050311 dated Mar. 3, 2020 [PCT/ISA/210].

* cited by examiner

*Primary Examiner* — Amy C Bonaparte
(74) *Attorney, Agent, or Firm* — Sughrue Mion, PLLC

(57) ABSTRACT

A composition for producing an N-vinylcarboxylic acid amide includes (A) an N-(1-alkoxyethyl)carboxylic acid amide and (B) a carboxylic acid amide other than the N-(1-alkoxyethyl)carboxylic acid amide and the N-vinylcarboxylic acid amide, and satisfies the following conditions: (1) the composition has a melting point of 0 to 30° C.; (2) a water content is 0 to 1.00% by mass in a total amount of the composition; (3) a content ratio of the component (A) to the component (B) is 4.0 to 20.0 in terms of a molar ratio; and (4) a 5% by mass aqueous solution of the composition has a pH of 4.0 to 8.0. A method for producing an N-vinylcarboxylic acid amide includes thermally decomposing or catalytically decomposing the composition for producing an N-vinylcarboxylic acid amide.

9 Claims, No Drawings

COMPOSITION FOR PRODUCING N-VINYL CARBOXYLIC ACID AMIDE

CROSS REFERENCE TO RELATED APPLICATIONS

This application is a National Stage of International Application No. PCT/JP2019/050311 filed on Dec. 23, 2019, claiming priority based on Japanese Patent Application No. 2018-246081 filed on Dec. 27, 2018.

TECHNICAL FIELD

The present invention relates to a composition to be used for producing an N-vinylcarboxylic acid amide, the composition comprising an N-(1-alkoxyethyl)carboxylic acid amide, and a method for producing an N-vinylcarboxylic acid amide using the composition.

BACKGROUND ART

A large number of methods for producing an N-vinylcarboxylic acid amide have been proposed so far. Examples of the methods include a method in which an N-(1-alkoxyethyl)carboxylic acid amide to be an intermediate is produced using a carboxylic acid amide, acetaldehyde, and an alcohol as raw materials, and thereafter the N-(1-alkoxyethyl)carboxylic acid amide is thermally decomposed or catalytically decomposed to synthesize the N-vinylcarboxylic acid amide. Generally, when a polymerizable monomer is produced, it is important to produce the polymerizable monomer without polymerizing a synthesized monomer as much as possible in the processes. Therefore, a highly polymerizable compound, such as acrylic acid, is produced using a polymerization inhibitor, and a polymerization inhibitor is added also in the product. On the other hand, when some polymerizable monomers, such as N-vinylcarboxylic acid amide not containing a polymerization inhibitor are industrially produced, process control, such as performing production through a highly stable intermediate or performing production at a temperature as low as possible, is important.

Some proposals have been made so far on an influence of an N-(1-alkoxyethyl)carboxylic acid amide on the product quality of an N-vinylcarboxylic acid amide in the production of the N-vinylcarboxylic acid amide. For example, Patent Literature 1 specifies the content of a metal component in an N-(1-alkoxyethyl)carboxylic acid amide. The literature describes the amount of a polymerization inhibiting substance generated in the produced N-vinylcarboxylic acid amide.

CITATION LIST

Patent Literature

PTL1: JP 2002-167369 A

SUMMARY OF INVENTION

Technical Problem

An N-vinylcarboxylic acid amide can be synthesized by thermally decomposing or catalytically decomposing an N-(1-alkoxyethyl)carboxylic acid amide being an intermediate, or by other methods. However, when raw material components comprising an N-(1-alkoxyethyl)carboxylic acid amide are supplied to a decomposition step, the raw material components solidify in piping due to failure of a temperature control mechanism for supply piping, or the like, or a reaction product generated by an unintended reaction, such as denaturation, side reaction, or polymerization, due to heating in the decomposition step adheres in equipment piping or an apparatus in some cases, and in the worst case, there has been a possibility that a problem of a production stop due to clogging of piping or the like occurs. In addition, to prevent the occurrence of such failure, measures in facilities or process control have been required, such as, for example, performing production through a highly stable intermediate, improving a thermal decomposition device or supply piping, and introducing temperature control facilities with superior performance, and many restrictions in terms of production facilities and operation have existed.

In Patent Literature 1 described above, the amount of the polymerization inhibiting substance generated in the produced N-vinylcarboxylic acid amide has been studied, but a relationship between the raw material components and the stability of production during producing the N-vinylcarboxylic acid amide has not been studied.

As described herein, with respect to the production of an N-vinylcarboxylic acid amide, an influence of a composition comprising an N-(1-alkoxyethyl)carboxylic acid amide which is a precursor on the stability of production has hardly been studied so far.

The present invention has been made in such circumstances, and an object of the present invention is to provide a composition for producing an N-vinylcarboxylic acid amide, the composition enabling more stable production in the production of the N-vinylcarboxylic acid amide.

Solution to Problem

The present inventors have paid attention to the aspect of an N-(1-alkoxyethyl)carboxylic acid amide-containing composition to be supplied to a thermal decomposition or catalytic decomposition step in production of an N-vinylcarboxylic acid amide and an influence of the composition on the stability of the production of the N-vinylcarboxylic acid amide to find that the problems can be solved by using the composition satisfying particular conditions.

The present invention have been completed based on such findings.

That is, the present invention relates to the following [1] to [10].

[1] A composition for producing an N-vinylcarboxylic acid amide, the composition comprising: component (A) which is an N-(1-alkoxyethyl)carboxylic acid amide; and component (B) which is a carboxylic acid amide other than the N-(1-alkoxyethyl)carboxylic acid amide and the N-vinylcarboxylic acid amide, and satisfying the following conditions of (1) to (4).
 (1) the composition has a melting point of 0 to 30° C.
 (2) a water content is 0 to 1.00% by mass in a total amount of the composition
 (3) a content ratio of the component (A) to the component (B) is 4.0 to 20.0 in terms of a molar ratio
 (4) a 5% by mass aqueous solution of the composition has a pH of 4.0 to 8.0
[2] The composition for producing an N-vinylcarboxylic acid amide according to [1], wherein the component (A) is a compound represented by the following formula (I):

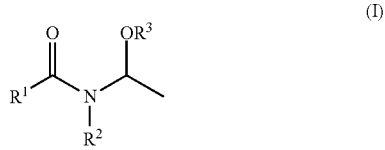

wherein $R^1$ represents an alkyl group having 1 to 5 carbon atoms, $R^2$ represents a hydrogen atom or an alkyl group having 1 to 5 carbon atoms, and $R^3$ represents an alkyl group having 1 to 5 carbon atoms.

[3] The composition for producing an N-vinylcarboxylic acid amide according to [1] or [2], wherein the component (B) is a compound represented by the following formula (II):

wherein $R^1$ represents an alkyl group having 1 to 5 carbon atoms, $R^2$ represents a hydrogen atom or an alky group having 1 to 5 carbon atoms.

[4] The composition for producing an N-vinylcarboxylic acid amide according to any one of [1] to [3], wherein the component (A) is an N-(1-methoxyethyl)carboxylic acid amide.

[5] The composition for producing an N-vinylcarboxylic acid amide according to any one of [1] to [4], wherein the component (A) is N-(1-methoxyethyl)acetamide.

[6] The composition for producing an N-vinylcarboxylic acid amide according to any one of [1] to [5], wherein the component (B) is acetamide.

[7] The composition for producing an N-vinylcarboxylic acid amide according to any one of [1] to [6], wherein a residual ratio (%) of the component (A) in the composition after retaining the composition under a condition of 160° C. at normal pressure in the atmosphere for 4 hours is 70% or more.

[8] The composition for producing an N-vinylcarboxylic acid amide according to any one of [1] to [7], wherein a content of the component (A) in a total amount of the composition is 70.0 to 96.0% by mass.

[9] The composition for producing an N-vinylcarboxylic acid amide according to any one of [1] to [8], wherein a total content of the component (A) and the component (B) in a total amount of the composition is 75.0 to 99.0% by mass.

[10] A method for producing an N-vinylcarboxylic acid amide, comprising thermally decomposing or catalytically decomposing the composition for producing an N-vinylcarboxylic acid amide according to any one of [1] to [9].

Advantageous Effects of Invention

According to the present invention, a composition for producing an N-vinylcarboxylic acid amide, the composition enabling more stable production in the production of the N-vinylcarboxylic acid amide, can be provided.

DESCRIPTION OF EMBODIMENTS

Hereinafter, the present invention will be described in detail, but the present invention is not limited to the following embodiments.

In addition, with respect to preferred numerical value ranges (such as, for example, ranges of a content) used herein, the lower limit values and the upper limit values described stepwise can independently be combined. For example, from the description "preferably 10 to 90, more preferably 30 to 80, and still more preferably 40 to 70", a range of, for example, "10 to 70", "30 to 70", or "40 to 80", in which a lower limit value and an upper limit value each selected independently are combined, can also be selected as a preferred range. Moreover, from the same description, a range of, for example, "40 or more" or "70 or less", in which only one of the lower limit value and the upper limit value is specified, can also be selected. Further, the same applies to a preferred range which can be selected from the description, such as, for example, "preferably 10 or more, more preferably 30 or more, and still more preferably 40 or more, and preferably 90 or less, more preferably 80 or less, and still more preferably 70 or less".

[Composition for Producing N-Vinylcarboxylic Acid Amide]

A composition for producing an N-vinylcarboxylic acid amide of the present invention is a composition (hereinafter, also simply referred to as "composition") comprising: component (A) which is an N-(1-alkoxyethyl)carboxylic acid amide (hereinafter, also simply referred to as "component (A)"); and component (B) which is a carboxylic acid amide other than the N-(1-alkoxyethyl)carboxylic acid amide and the N-vinylcarboxylic acid amide (hereinafter, also simply referred to as "component (B)") and satisfies the following conditions of (1) to (4).

(1) the composition has a melting point of 0 to 30° C.
(2) a water content is 0 to 1.00% by mass in the total amount of the composition
(3) a content ratio of the component (A) to the component (B) is 4.5 to 20.0 in terms of a molar ratio
(4) a 5% by mass aqueous solution of the composition has a pH of 4.0 to 8.0

Component (A): N-(1-Alkoxyethyl)carboxylic Acid Amide

Preferred examples of the component (A) to be used in the present invention which is the N-(1-alkoxyethyl)carboxylic acid amide include a compound represented by the following formula (I):

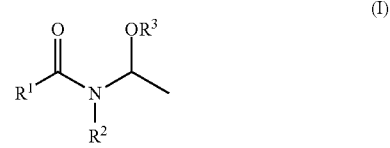

and more preferably an N-(1-methoxyethyl)carboxylic acid amide.

In formula (I), $R^1$ represents an alkyl group having 1 to 5 carbon atoms, preferably an alkyl group having 1 to 3 carbon atoms, more preferably a methyl group or an ethyl group, and still more preferably a methyl group. $R^2$ represents a hydrogen atom or an alkyl group having 1 to 5 carbon atoms, preferably a hydrogen atom or an alkyl group having 1 to 3 carbon atoms, more preferably a hydrogen atom or a methyl group, and still more preferably a hydrogen atom. $R^3$ represents an alkyl group having 1 to 5 carbon atoms, preferably an alkyl group having 1 to 3 carbon atoms, more preferably a methyl group or an ethyl group, and still more preferably a methyl group.

Examples of the compound represented by formula (I) include N-(1-methoxyethyl)acetamide, N-(1-methoxyethyl)-N-methylacetamide, N-(1-ethoxyethyl)acetamide, N-(1-ethoxyethyl)-N-methylacetamide, N-(1-propoxyethyl)acetamide, N-(1-isopropoxyethyl)acetamide, N-(1-butoxyethyl)acetamide, N-(1-isobutoxyethyl)acetamide, N-(1-methoxyethyl)propionamide, N-(1-ethoxyethyl)propionamide, N-(1-propoxyethyl)propionamide, N-(1-isopropoxyethyl)propionamide, N-(1-butoxyethyl)propionamide, N-(1-isobutoxyethyl)propionamide, N-(1-methoxyethyl)butyramide, N-(1-ethoxyethyl)butyramide, N-(1-propoxyethyl)butyramide, N-(1-isopropoxyethyl)butyramide, N-(1-butoxyethyl)butyramide, N-(1-isobutoxyethyl)butyramide, N-(1-methoxyethyl)isobutyramide, N-(1-ethoxyethyl)isobutyramide, N-(1-propoxyethyl)isobutyramide, N-(1-isopropoxyethyl)isobutyramide, N-(1-butoxyethyl)isobutyramide, and N-(1-isobutoxyethyl)isobutyramide. Among these, preferred examples include N-(1-methoxyethyl)acetamide, N-(1-isopropoxyethyl)acetamide, and N-(1-methoxyethyl)isobutyramide, and more preferred examples include N-(1-methoxyethyl)acetamide.

Examples of methods for synthesizing component (A) which can be used in the present invention include, but not particularly limited to: a condensation reaction of acetaldehyde, component (A), and the carboxylic acid amide other than the N-vinylcarboxylic acid amide, and an alcohol using an acid catalyst; a substitution reaction of an acetaldehyde acetal with component (A) and the carboxylic acid amide other than the N-vinylcarboxylic acid amide using an acid catalyst; and a condensation reaction of acetaldehyde with component (A) and the carboxylic acid amide other than the N-vinylcarboxylic acid amide using a base, and a subsequent condensation reaction with an alcohol using an acid catalyst.

Examples of the alcohol which is used in these reactions include an alcohol represented by $R^3$—OH. $R^3$ represents an alkyl group having 1 to 5 carbon atoms, preferably an alkyl group having 1 to 3 carbon atoms, more preferably a methyl group or an ethyl group, and still more preferably a methyl group. That is, the alkyl group represented by the $R^3$ corresponds to the alkyl group constituting $R^3$ in the previously mentioned compound represented by formula (I).

The acid catalyst may be any of a homogeneous catalyst and a heterogeneous catalyst, and examples of the homogeneous catalyst include: mineral acids, such as hydrochloric acid, sulfuric acid, nitric acid, and phosphoric acid; heteropoly acids, such as phosphotungstic acid; and organic acids, such as methanesulfonic acid and p-toluic acid. Further, a salt of a strong acid and a weak base can also be used even though the salt does not necessarily dissolve uniformly. Examples of the salt of a strong acid and a weak base include ammonium sulfate and ammonium chloride. Examples of the heterogeneous catalyst include a gel-type or porous-type acidic ion-exchange resin.

Examples of the base catalyst include inorganic bases, such as lithium hydroxide, sodium hydroxide, potassium hydroxide, cesium hydroxide, sodium carbonate, potassium carbonate, cesium carbonate, sodium bicarbonate, potassium bicarbonate, cesium bicarbonate, sodium phosphate, potassium phosphate, sodium monohydrogen phosphate, potassium monohydrogen phosphate, sodium pyrophosphate, and potassium pyrophosphate; organic amines, such as triethylamine, pyridine, and morpholine; and ion-exchange resins.

When component (A) is synthesized using an acid catalyst, a reaction solution containing the N-(1-alkoxyethyl)carboxylic acid amide obtained by the synthesis is neutralized to a pH of preferably 8.0 to 8.5 with a base, and the N-(1-alkoxyethyl)carboxylic acid amide is thereafter purified.

The method for purifying component (A) is not particularly limited, but purification by distillation is preferable from the viewpoint of separation from impurities. Examples of the distillation method include a single distillation method and a precision distillation method with a distillation apparatus equipped with a rectifying column. The apparatus for performing distillation by a single distillation method is not particularly limited, but as a measure for suppressing an increase in impurities in the distillate with accompanying of mist, it is effective to install a mist separator or the like in a gas line. Component (A) undergoes denaturation due to heat in some cases, and therefore a thermal history is preferably avoided as much as possible. Thus, the distillation is preferably performed under a condition of a temperature of 100° C. or lower at a pressure of preferably 0.1 to 1.3 kPa (absolute pressure), more preferably 0.1 to 0.5 kPa (absolute pressure), and still more preferably 0.1 to 0.4 kPa (absolute pressure) while low-boiling-point components are being removed by distillation appropriately.

A content of the component (A) in the total amount of the composition is preferably 70.0 to 96.0% by mass, more preferably 75.0 to 92.0% by mass, and still more preferably 78.0 to 88.0% by mass. The content is measured by the method described in Examples below.

Component (B): Carboxylic Acid Amide Other Than N-(1-Alkoxyethyl)carboxylic Acid Amide and N-Vinylcarboxylic Acid Amide The component (B) to be used in the present invention which is a carboxylic acid amide is a carboxylic acid amide other than the N-(1-alkoxyethyl)carboxylic acid amide and the N-vinylcarboxylic acid amide. Preferred examples of the component (B) include a compound represented by the following formula (II).

(II)

In formula (II), $R^1$ represents an alkyl group having 1 to 5 carbon atoms, preferably an alkyl group having 1 to 3 carbon atoms, more preferably a methyl group or an ethyl group, and still more preferably a methyl group. $R^2$ represents a hydrogen atom or an alkyl group having 1 to 5 carbon atoms, preferably a hydrogen atom or an alkyl group having 1 to 3 carbon atoms, more preferably a hydrogen atom or a methyl group, and still more preferably a hydrogen atom.

Examples of the compound represented by formula (II) include acetamide and N-alkyl derivatives thereof, propionamide and N-alkyl derivatives thereof, butyramide and N-alkyl derivatives thereof, and isobutyramide and N-alkyl derivatives thereof, preferred examples include acetamide and N-alkyl derivatives thereof and isobutyramide and N-alkyl derivatives thereof, more preferred examples include acetamide and isobutyramide, and still more preferred examples include acetamide.

A content of the component (B) in the total amount of the composition is preferably 1.0 to 15.0% by mass, more preferably 1.5 to 10.0% by mass, and still more preferably 2.0 to 9.5% by mass.

In addition, a total content of the component (A) and the component (B) in the total amount of the composition is preferably 75.0 to 99.0% by mass, more preferably 80.0 to 98.0% by mass, and still more preferably 85.0 to 98.0% by mass.

Usually, a composition for producing an N-vinylcarboxylic acid amide is prepared in such a way that the total content is made closer to 100% by mass, and component (A) is contained in high purity, from the viewpoint of improving the yield of the N-vinylcarboxylic acid amide. However, in the case of the composition of the present invention, a suitable upper limit value of the total content may be a previously mentioned value, from the viewpoint that restrictions on the production facilities in synthesizing and purifying the N-(1-alkoxyethyl)carboxylic acid amide-containing composition can be reduced as will be mentioned later in the description of the following condition (3), and the N-vinylcarboxylic acid amide can stably be produced.

Each of these contents is measured by the method described in Examples below.

<Condition (1)>

The composition of the present invention has a melting point of 0 to 30° C. When the melting point is higher than 30° C., there is a need to control the piping temperature in such a way as to be higher than 30° C. in order to, for example, prevent solidification of the composition in piping from which the composition is transferred to the next step when the N-vinylcarboxylic acid amide is produced. In addition, for example, when the temperature of piping is kept, or controlled with a heater or the like, the possibility that the composition solidifies increases at some parts where the temperature control is insufficient, some parts where piping is thin, or the like depending on the type of heat insulating material or heater. When the melting point is lower than 0° C., the composition is made insufficient in terms of product quality. Here, the term "the composition is made insufficient in terms of product quality" refers to, for example, that a composition with which the final yield of the N-vinylcarboxylic acid amide is lowered is made. Examples of such a composition include a composition in which separation of low-boiling-point components in the composition is insufficient and, as a result, the concentration of the amount of the component (A) contained is lowered.

From such a viewpoint, the melting point is preferably 0 to 20° C., more preferably 5 to 15° C., and still more preferably 8 to 13° C.

The melting point is measured by the method described in Examples below.

It is to be noted that the melting point is influenced by the formation of the composition. For example, there is a tendency that when the content of the component (A) increases, the value of the melting point becomes higher.

<Condition (2)>

The composition of the present invention has a water content (hereinafter, also referred to as "moisture") of 0 to 1.00% by mass in the total amount of the composition. If the moisture is more than 1.00% by mass, for example, the component (A) is easily decomposed into the component (B), acetaldehyde, and an alcohol when the composition is heated in a vaporizer, as will be mentioned later, and the thermal stability of the composition is lowered. As a result, an unintended reaction, such as denaturation, side reaction, or polymerization of the composition, occurs in a heating step with a vaporizer or the like, so that a possibility leading to a trouble, such as clogging of the production apparatus or lowering of the yield or the product quality of the N-vinylcarboxylic acid amide, increases.

When the composition contains water, the water is mainly water derived from the raw materials or the like for the component (A) or water generated or mixed in the process of synthesis.

From such a viewpoint, the water content is preferably 0 to 0.50% by mass in the total amount of the composition, more preferably 0.01 to 0.30% by mass in the total amount of the composition, and still more preferably 0.01 to 0.20% by mass in the total amount of the composition.

The water content is measured by the method described in Examples below.

<Condition (3)>

The composition of the present invention has a content ratio of the component (A) to the component (B) of 4.0 to 20.0 in terms of a molar ratio. When the molar ratio is lower than 4.0, the ratio of the component (B) to the component (A) increases, so that when the composition is heated with a vaporizer or the like, the progress of a side reaction in which the component (A) and the component (B) reacts to generate by-products is likely to occur. When the molar ratio is higher than 20, the melting point of the composition becomes higher, so that a possibility of solidification of the composition in piping, such as supply piping, at the time of producing the N-vinylcarboxylic acid amide, or the like increases.

From such a viewpoint, the molar ratio is preferably 4.2 to 15.0, more preferably 4.5 to 9.0, and still more preferably 4.8 to 8.0.

In addition, from the viewpoint of improving the yield of the N-vinylcarboxylic acid amide, the composition comprising the component (A) in high purity is usually used. However, to obtain the composition comprising the component (A) in high purity, it is effective to reduce the concentration of the carboxylic acid amide other than the N-(1-alkoxyethyl)carboxylic acid amide and the N-vinylcarboxylic acid amide, which is the raw material, but, in the case of a batch reaction, productivity is lowered, and in the case of a large production scale in continuous synthesis facilities or the like, large capital investment is required. In addition, when the component (A) is highly purified, a multistage distillation column is needed in order to separate the component (B) having a boiling point close to that of the component (A), so that large capital investment is also required in this case. However, the present inventors have found that when the molar ratio is 20.0 or less, the previously mentioned disadvantages can be avoided. Therefore, the molar ratio is preferably 15.0 or less, more preferably 9.0 or less, and still more preferably 8.0 or less, also from the viewpoint of improving the operation stability at the time of producing the N-vinylcarboxylic acid amide, enabling, as a result, reduction in production costs by contributing to an improvement in continuous operability and further, from the viewpoint of enabling production with simpler production facilities.

The molar ratio is measured by the method described in Examples below.

<Condition (4)>

A 5% by mass aqueous solution of the composition of the present invention has a pH of 4.0 to 8.0. If the pH is lower than 4, the progress of a side reaction in which the component (A) and the component (B) reacts to generate by-products is likely to occur when the composition is heated by a vaporizer or the like. It is to be noted that in a region where pH is 8.0 or higher, the progress of the side reaction is unlikely to occur when the neutralization step in synthesizing the component (A) is performed at a pH of 8.0 to 8.5, which is the preferred range mentioned previously, in the method for obtaining the composition.

From such a viewpoint, the 5% by mass aqueous solution of the composition preferably has a pH of 4.3 to 7.8, more preferably 4.5 to 7.6, and still more preferably 5.0 to 7.5.

The pH of the 5% by mass aqueous solution of the composition is measured by the method described in Examples below.

It is to be noted that pH of the 5% by mass aqueous solution of the composition is influenced by the formation of the composition. For example, pH of the 5% by mass aqueous solution of the composition is influenced by the type and the amount of the acid catalyst which is used when the component (A) is synthesized and the base which is used in the neutralization step. Therefore, if the formations other than the acid catalyst and the base which is used in neutralization are the same, the value of the pH is higher when pH of the reaction solution comprising the component (A) is adjusted to a higher value in the neutralization step in synthesizing the component (A).

Other Components

The composition may comprise other components within a range not impairing the effects of the present invention. Examples of such components include a component derived from each compound which is used when the component (A) is produced, or a decomposed product or a by-product of the synthesized the component (A). Examples of other components include: an alcohol, such as methanol, which is used as a solvent or a raw material component which is used in a synthesis reaction; an acetaldehyde acetal, such as an acetaldehyde dialkyl acetal; an ethylidene biscarboxylic acid amide; or an N-vinylcarboxylic acid amide which is generated by decomposition or the like when the N-(1-alkoxyethyl)carboxylic acid amide is purified and separated by distillation or the like.

[Method for Producing N-Vinylcarboxylic Acid Amide]

As mentioned previously, the composition is used for producing the N-vinylcarboxylic acid amide. The N-vinylcarboxylic acid amide can be synthesized by performing known thermal decomposition or catalytic decomposition on the composition. Examples of the conditions at the time when these types of decomposition are performed include a reaction temperature of 60 to 600° C., a reaction time of 0.3 seconds to 2 hours, an operation pressure of 0.1 kPa (absolute pressure) to the pressure of the atmosphere in a gas phase or a liquid phase. Among these conditions, the reaction is preferably performed under a condition of a reaction temperature of 300 to 600° C., a reaction time of 0.3 seconds to 1 minute, and an operation pressure of 10 to 30 kPa (absolute pressure) in a gas phase.

The composition can be decomposed into the N-vinylcarboxylic acid amide and an alcohol by, for example, feeding the composition in a liquid state into a vaporizer to vaporize the composition with the vaporizer of a pressure of 10 to 30 kPa (absolute pressure) and 120 to 200° C. and then supplying the vaporized composition into a thermal decomposition apparatus of a reaction temperature of 300 to 600° C.

The vaporizer is not particularly limited, but from the viewpoint of vaporizing the raw materials efficiently, preferred examples thereof include a falling liquid film evaporator and a forced liquid film evaporator.

In addition, a thermal decomposition reactor included in the thermal decomposition apparatus preferably has a tubular structure from the viewpoint of performing thermal decomposition of the vaporized raw materials efficiently.

From the viewpoint of feeding the composition as liquid in this way, when the liquid state can be retained (for example, at normal temperature) so that solidification will not occur in piping even though the composition is influenced by the temperature around piping if, for example, failure occurs in the temperature control of piping, it is considered that solidification of the raw materials in piping can be prevented. In this respect, the composition of the present invention satisfies the melting point of condition (1) and can therefore prevent solidification in piping even if failure occurs in the temperature control of piping, as mentioned previously.

In addition, when the composition has sufficient thermal stability in the vaporizer, the supplied composition is vaporized almost completely and supplied to the next reaction step, and therefore a possibility that failure related to an apparatus occurs is lowered even when continuous operation is performed. However, if the thermal stability of the composition is insufficient, and the composition undergoes denaturation, side reaction, polymerization, or the like in the vaporizer to generate a by-product that is solid even at a high temperature, a possibility that the by-product leads to clogging of the apparatus increases. This is not only limited to the vaporizer, but the same applies to facilities that heat the composition in the process of synthesizing the N-vinylcarboxylic acid amide.

From such a viewpoint, the composition preferably has a residual ratio of the component (A) of 70% or more, more preferably 75% or more, and still more preferably 80% or more, the residual ratio calculated by the method described in Examples below.

In addition, the thermal stability of the composition is also influenced by the moisture and the content ratio (molar ratio) of the component (A) to the component (B) in the composition, pH of the 5% by mass aqueous solution, and the like, and also varies depending on the combination of these conditions. Therefore, in a certain aspect, the component (A) causes reaction such as denaturation, side reaction, or polymerization in no small way due to heating when the residual ratio of the component (A), which is calculated by the method described in Examples below is evaluated, and therefore from such a viewpoint, a suitable upper limit value of the residual ratio may be, for example, 85%, 90%, or 95%.

<N-Vinylcarboxylic Acid Amide>

Preferred examples of the N-vinylcarboxylic acid amide which is produced using the composition of the present invention include a compound represented by the following formula (III).

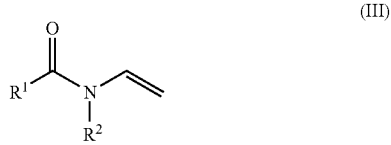

(III)

In formula (III), $R^1$ represents an alkyl group having 1 to 5 carbon atoms, preferably an alkyl group having 1 to 3 carbon atoms, more preferably a methyl group or an ethyl group, and still more preferably a methyl group. $R^2$ represents a hydrogen atom or an alkyl group having 1 to 5 carbon atoms, preferably a hydrogen atom or an alkyl group having 1 to 3 carbon atoms, more preferably a hydrogen atom or a methyl group, and still more preferably a hydrogen atom.

Examples of the compound represented by formula (III) include N-vinylacetamide, N-methyl-N-vinylacetamide, N-vinylpropionamide, N-methyl-N-vinylpropionamide, N-vinylisobutyramide, and N-methyl-N-vinylisobutyramide, preferred examples include N-vinylacetamide and N-vinylisobutyramide, and more preferred examples include N-vinylacetamide.

EXAMPLES

Hereinafter, the present invention will be described in more detail in reference with Examples, but the present invention is not limited to the following Examples as long as it falls within a range not exceeding the gist of the present invention.

The characteristics and the like of the compositions and each component were measured and evaluated by the following methods.

[Measurement of Moisture]

The moisture (water content) of the compositions was measured using a Karl Fischer coulometric titration method moisture measurement apparatus "CA-200" manufactured by Mitsubishi Chemical Analytech Co., Ltd.

[Content of Each Component and Content Ratio (Molar Ratio) of Component (A) to Component (B) in Compositions]

The content of each component excluding water in the compositions was determined quantitatively by gas chromatography (GC) analysis (internal standard method, internal standard substance: diethylene glycol dimethyl ether), and the content ratio (molar ratio) of component (A) to component (B) was calculated from the quantity of each component determined quantitatively.

The condition of the GC analysis is shown below.
Apparatus: high-performance general-purpose gas chromatograph "GC-2014" (manufactured by SHIMADZU CORPORATION)
Column: "HP-WAX" ($\phi$ 0.25 mm×30 m, manufactured by Agilent Technologies, Inc.)
Type of carrier gas: He
Flow rate of carrier gas: 1 mL/min
Split ratio: 40
Column temperature: a temperature increase program was set in the order of 40° C. (7 minutes)→temperature increase (25° C./min)→130° C. (15 minutes)→temperature increase (30° C./min)→220° C. (2 minutes)
Injection temperature: 200° C.
Detector: flame ionization detector (FID)
Detector temperature: 230° C.

[pH]

pH was measured at a sample temperature of 20 to 25° C. using a personal pH meter "PH71" (manufactured by Yokogawa Electric Corporation).

It is to be noted that the 5% by mass aqueous solutions of the compositions shown in Tables 1 and 2 each were prepared by adding pure water in such a way as to make the composition prepared in each Example into an aqueous solution having a concentration of the composition of 5% by mass.

[Melting Point]

The melting point of the compositions was measured by filling a glass thin tube provided with a thermometer with each composition, which is a measurement sample, thereafter immersing the glass tube in a water bath adjusted to 0° C. using ice water, and increasing the temperature of a temperature-controlled circulation tank at 5° C./h. The point at which the solid began to melt and liquid can be recognized was determined as the melting point.

[Evaluation of Thermal Stability of Compositions]

The thermal stability of the compositions was evaluated using the following method.

20 g of the composition prepared in each Example was charged into a three-necked flask having an internal volume of 50 mL, a stirrer was placed therein, and the composition was stirred and heated for 4 hours under a condition of 160° C. at normal pressure in the atmosphere. In the three-necked flack, an insertion tube for a thermometer was installed, and components distilled out by heating were collected through a cooling pipe. From the content of component (A) which is the N-(1-alkoxyethyl)carboxylic acid amide in the composition after the heat treatment, and the content of component (A) in the composition before the heat treatment, the residual ratio (%) of component (A) which is the N-(1-alkoxyethyl) carboxylic acid amide was calculated using the following equation.

Residual ratio (%) of N-(1-alkoxyethyl)carboxylic acid amide=[[weight of composition after heat treatment×concentration of N-(1-alkoxyethyl) carboxylic acid amide in composition after heat treatment]/[weight of composition before heat treatment×concentration of N-(1-alkoxyethyl) carboxylic acid amide in composition before heat treatment]]×100(%)

It is to be noted that the concentration of the N-(1-alkoxyethyl)carboxylic acid amide before and after the heat treatment was checked using the same method as that of the previously mentioned GC analysis.

[Acetic Acid Concentration]

The acetic acid concentration of the reaction solution described in Comparative Example 1 was checked using the same method as that of the previously mentioned GC analysis.

Example 1

<Synthesis Example 1-1> (Synthesis of Acetaldehyde Dimethyl Acetal)

After 6.6 g of sulfuric acid was added to 420 g of methanol, and a resultant mixture was cooled to 0° C., 230 g of acetaldehyde was added to synthesize a solution containing acetaldehyde dimethyl acetal as a main component. And a yield of the acetaldehyde dimethyl acetal was 75%. This solution was used in Synthesis Example 1-2 described below without being purified.

<Synthesis Example 1-2> (Synthesis of N-(1-Methoxyethyl)acetamide)

After a mixed solution in which 337 g of methanol, 300 g of acetaldehyde, and 230 g of acetamide was mixed was prepared, 640 g of the acetaldehyde dimethyl acetal-containing solution obtained in Synthesis Example 1-1 was added to the mixed solution at 40° C., and a resultant mixture was thereafter reacted for 6 hours to obtain a reaction solution having a pH of 1.2. Thereafter, a 48% by mass aqueous solution of sodium hydroxide was added to this reaction solution to obtain an N-(1-methoxyethyl)acetamide-containing solution having a pH adjusted to 8.3.

<Preparation Example 1> (Preparation of N-(1-Methoxyethyl)acetamide-Containing Composition)

From the N-(1-methoxyethyl)acetamide-containing solution having a pH of 8.3 which was obtained in Synthesis Example 1-2, low-boiling-point components, such as acetaldehyde and acetaldehyde dimethyl acetal, were distilled away using a single distillation apparatus under a condition of a temperature of 60 to 70° C. and a pressure of 33 kPa (absolute pressure). Furthermore, water and methanol were thereafter distilled away under a condition of a temperature of 70° C. and a pressure of 0.3 kPa (absolute pressure) to obtain a concentrated solution.

The resultant concentrated solution was further distilled under reduced pressure to obtain 345 g of a fraction in a range of a temperature of 80 to 100° C. (pressure of 0.3 kPa (absolute pressure)) as a composition comprising 78.3% by mass of N-(1-methoxyethyl)acetamide and 7.7% by mass of acetamide.

The resultant N-(1-methoxyethyl)acetamide-containing composition had a melting point=8° C., a moisture=0.10% by mass, a molar ratio of N-(1-methoxyethyl)acetamide to acetamide=5.1, and a pH of a 5% by mass aqueous solution=4.3. In addition, the residual ratio of N-(1-methoxyethyl)acetamide obtained by the evaluation of the thermal stability was 75.1%. Evaluation results of the resultant composition are shown in Table 1 below.

<Synthesis Example 1-3> (Synthesis of N-Vinylacetamide)

The N-(1-methoxyethyl)acetamide-containing composition obtained in Preparation Example 1 was supplied at a supply rate of 1.5 g/min to a vaporizer (having an inner diameter of 20 mm and a length of 240 mm) kept at 160° C. and 20 kPa (absolute pressure) through supply piping the temperature of which was set at 30° C. to be vaporized, and was thereafter introduced in a vaporized state into a reactor (a tubular reactor having an inner diameter of 20 mm and a length of 240 mm) of 400° C. and 20 kPa (absolute pressure) to be thermally decomposed.

A mixture of N-vinylacetamide and methanol generated by the thermal decomposition reaction was condensed with a cooling pipe installed at the reactor outlet to collect crude N-vinylacetamide. A production trouble, such as solidification of supplied raw materials in the supply piping or clogging of the apparatus due to generation of a by-product in the vaporizer, or the like was not ascertained at the time of the thermal decomposition reaction, therefore the thermal decomposition reaction was satisfactory, and N-vinylacetamide was obtained with a yield of 90%.

Example 2

After 482 of the low-boiling-point components (69% by mass of acetaldehyde dimethyl acetal, 16% by mass of acetaldehyde, 13% by mass of methanol, and 2% by mass of water) collected by the distillation of the N-(1-methoxyethyl)acetamide-containing solution having a pH of 8.3 which was obtained in Synthesis Example 1-2 of Preparation Example 1 of Example 1, 240 g of acetamide, and 312 g of acetaldehyde were mixed and warmed to 40° C., a solution obtained by dissolving 15 g of sulfuric acid in 460 g of methanol was added thereto, and a resultant mixture was reacted for 6 hours to obtain a reaction solution having a pH of 1.1. Thereafter, a 48% by mass sodium hydroxide aqueous solution was added to this reaction solution to obtain an N-(1-methoxyethyl)acetamide-containing solution having a pH adjusted to 8.3. The same operation as in Preparation Example 1 of Example 1 was performed on the N-(1-methoxyethyl)acetamide-containing solution to obtain an N-(1-methoxyethyl)acetamide-containing composition. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 3

An N-(1-methoxyethyl)acetamide-containing composition was obtained by performing operation in the same manner as in Example 2, except that the amount of acetamide mixed in Example 2 was changed to 217 g. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 4

An N-(1-methoxyethyl)acetamide-containing composition was obtained by performing operation in the same manner as in Example 2, except that the amount of acetamide mixed in Example 2 was changed to 197 g. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 5

An N-(1-methoxyethyl)acetamide-containing composition was obtained by performing operation in the same manner as in Example 2, except that the amount of acetamide mixed in Example 2 was changed to 181 g. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 6

After 50 g of acetamide, 700 g of acetaldehyde dimethyl acetal, and 150 g of acetaldehyde were mixed and warmed to 40° C., a solution obtained by dissolving 10 g of sulfuric acid in 180 g of methanol was added thereto, and a resultant mixture was reacted for 6 hours to obtain a reaction solution having a pH of 1.2. Thereafter, a 48% by mass aqueous solution of sodium hydroxide was added to this reaction solution to obtain an N-(1-methoxyethyl)acetamide-containing solution having a pH adjusted to 8.3.

An N-(1-methoxyethyl)acetamide-containing composition was obtained by performing the same operation as in Preparation Example 1 of Example 1 on the N-(1-methoxyethyl)acetamide-containing solution. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 7

After 50 g of acetamide, 1000 g of acetaldehyde dimethyl acetal, and 170 g of acetaldehyde were mixed and warmed to 40° C., a solution obtained by dissolving 14 g of sulfuric acid in 200 g of methanol was added thereto, and a resultant mixture was reacted for 6 hours to obtain a reaction solution having a pH of 1.1. Thereafter, a 48% by mass aqueous solution of sodium hydroxide was added to this reaction solution to obtain an N-(1-methoxyethyl)acetamide-containing solution having a pH adjusted to 8.3.

An N-(1-methoxyethyl)acetamide-containing composition was obtained by performing the same operation as in Preparation Example 1 of Example 1 on the N-(1-methoxyethyl)acetamide-containing solution. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 8

Pure water was additionally added to the N-(1-methoxyethyl)acetamide-containing composition obtained in the same manner as in Example 2 to obtain a composition having a moisture adjusted to 0.5% by mass. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Example 9

Pure water was additionally added to the N-(1-methoxyethyl)acetamide-containing composition obtained in the same manner as in Example 3 to obtain a composition having a moisture adjusted to 0.96% by mass. Evaluation results of the resultant composition are shown in Table 1 below.

N-vinylacetamide was synthesized in the same manner as in Synthesis Example 1-3 of Example 1, except that the composition obtained in Example 8 was used, and no production trouble in the thermal decomposition step was ascertained.

Example 10

After 50 g of acetamide, 310 g of acetaldehyde dimethyl acetal, and 140 g of acetaldehyde were mixed and warmed to 40° C., a solution obtained by dissolving 10 g of sulfuric acid in 160 g of methanol was added thereto, and a resultant mixture was reacted for 6 hours to obtain a reaction solution having a pH of 1.2. Thereafter, a 48% by mass aqueous solution of sodium hydroxide was added to this reaction solution to obtain an N-(1-methoxyethyl)acetamide-containing solution having a pH adjusted to 8.3.

An N-(1-methoxyethyl)acetamide-containing composition was obtained by performing the same operation as in Preparation Example 1 of Example 1 on the N-(1-methoxyethyl)acetamide-containing solution. Evaluation results of the resultant composition are shown in Table 1 below.

N-vinylacetamide was synthesized in the same manner as in Synthesis Example 1-3 of Example 1, except that the composition was used, and no production trouble in the thermal decomposition step was ascertained.

Comparative Example 1

120 g of acetamide, 3680 g of acetaldehyde dimethyl acetal, and 200 g of methanol were mixed to prepare a uniform solution, which was used as a reaction raw material. A reaction tube having an inner diameter of 40 mm was filled with 60 mL of a strongly acidic ion-exchange resin "AMBERLYST (a registered trademark) 15", and the reaction tube was sunk in a warm water of 55° C. to set the reaction temperature to 55° C. The reaction raw material was introduced into this reaction tube at 5 mL per hour, a flowing-out reaction solution was collected and analyzed. The conversion ratio of acetamide was 98%, and the yield of N-(1-methoxyethyl)acetamide was 90%.

The resultant reaction solution was distilled with a single distillation apparatus to distill out low-boiling-point-components at 13 kPa (absolute pressure) and an oil bath temperature of 90° C., and pH of the still residue was measured to find that pH=4.3 and the acetic acid concentration was 430 ppm. After 1.1 equivalent of sodium carbonate based on acetic acid was added to this still residue, 207 g of an N-(1-methoxyethyl)acetamide-containing composition was distilled out at a pressure of 0.3 kPa (absolute pressure). In the resultant composition, the N-(1-methoxyethyl)acetamide content was 98.1% by mass, the acetamide content was 1.1% by mass, the melting point=32° C., the moisture=0.03% by mass, the molar ratio of N-(1-methoxyethyl)acetamide to acetamide=45.0, and pH of a 5% by mass aqueous solution=7.4. In addition, the residual ratio of N-(1-methoxyethyl)acetamide obtained by the thermal stability evaluation was 83.6%. Evaluation results of the resultant composition are shown in Table 2 below.

Synthesis of N-vinylacetamide was attempted in the same manner as in Synthesis Example 1-3 of Example 1, except that the composition was used, and as a result, a production trouble was ascertained in the thermal decomposition step by clogging due to solidification of the raw materials in raw material supply piping.

Comparative Examples 2 to 4

Pure water was additionally added to N-(1-methoxyethyl)acetamide-containing compositions obtained in the same manner as in Example 2 to obtain compositions each having a moisture adjusted to the content shown in Table 2 below. Evaluation results of each of the resultant compositions are shown in Table 2 below. The residual ratios of N-(1-methoxyethyl)acetamide obtained by the thermal stability evaluation were lowered in the order of Comparative Examples 2, 3, and 4 to 65.6%, 57.4%, and 47.5%.

N-vinylacetamide was synthesized in the same manner as in Synthesis Example 1-3 of Example 1, except that each composition obtained in Comparative Examples 2, 3, and 4 was used, and as a result, clogging of the vaporizer due to generation of a by-product was ascertained in the thermal decomposition step in any of Comparative Examples 2, 3, and 4.

Comparative Example 5

An N-(1-methoxyethyl)acetamide-containing composition was obtained by performing operation in the same manner as in Example 2, except that the reaction time for synthesizing N-(1-methoxyethyl)acetamide in Example 2 was changed from 6 hours to 2 hours. Evaluation results of the resultant composition are shown in Table 2 below.

N-vinylacetamide was synthesized in the same manner as in Synthesis Example 1-3 of Example 1, except that the composition was used, and as a result, clogging of the vaporizer was ascertained in the thermal decomposition step.

Comparative Example 6

An N-(1-methoxyethyl)acetamide-containing composition was obtained by performing operation in the same manner as in Example 1, except that the pH value adjusted after synthesizing N-(1-methoxyethyl)acetamide in Synthesis Example 1-2 in Example 1 was changed from a pH of 8.3 to a pH of 7.5. Evaluation results of the resultant composition are shown in Table 2 below.

N-vinylacetamide was synthesized in the same manner as in Synthesis Example 1-3 of Example 1, except that the composition was used, and as a result, clogging of the vaporizer was ascertained in the thermal decomposition step.

TABLE 1

|  |  | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Formation | Component (A) (% by mass)*1 | 78.3 | 81.4 | 88.4 | 89.3 | 90.4 | 93.9 | 94.9 | 82.7 | 87.2 | 91.2 |
|  | Component (B) (% by mass)*2 | 7.7 | 5.9 | 9.2 | 6.6 | 6.4 | 4.1 | 2.4 | 5.9 | 8.9 | 5.2 |
|  | NVA (% by mass)*3 | 13.3 | 12.4 | 1.9 | 3.7 | 2.8 | 1.6 | 2.2 | 10.6 | 2.5 | 3.2 |
| Properties | Melting point (° C.) | 8 | 9 | 9 | 13 | 12 | 23 | 29 | 9 | 8 | 15 |
|  | Moisture (% by mass) | 0.10 | 0.12 | 0.13 | 0.04 | 0.08 | 0.11 | 0.13 | 0.50 | 0.96 | 0.21 |
|  | Molar ratio (—) *4 | 5.1 | 7.0 | 4.8 | 6.8 | 7.0 | 11.5 | 19.9 | 7.0 | 4.9 | 8.8 |
|  | pH (—) *5 | 4.3 | 4.4 | 5.0 | 7.0 | 5.9 | 5.4 | 6.2 | 4.1 | 4.8 | 6.7 |
|  | Component (A) residual ratio (%) *6 | 75.1 | 76.1 | 74.9 | 83.9 | 84.2 | 81.8 | 83.2 | 70.8 | 72.3 | 82.1 |
| Production trouble | Clogging of supply piping | Not occurred | Not occurred | Not occurred | Not occurred | Not occurred | Not occurred | Not occurred | Not occurred | Not occurred | Not occurred |
|  | Clogging of thermal decomposition column | Not occurred | Not occurred | Not occurred | Not occurred | Not occurred | Not occurred | Not occurred | Not occurred | Not occurred | Not occurred |

*1Component (A): N-(1-methoxyethyl)acetamide
*2Component (B): acetamide
*3N-vinylacetamide
*4: Component (A)/Component (B) (molar ratio)
*5: pH of 5% by mass aqueous solution
*6: Thermal stability evaluation

TABLE 2

|  |  | Comparative Example 1 | Comparative Example 2 | Comparative Example 3 | Comparative Example 4 | Comparative Example 5 | Comparative Example 6 |
|---|---|---|---|---|---|---|---|
| Formation | Component (A) (% by mass) *1 | 98.1 | 82.1 | 81.1 | 78.8 | 77.9 | 78.8 |
|  | Component (B) (% by mass)*2 | 1.1 | 5.9 | 5.9 | 5.7 | 10.8 | 7.8 |
|  | NVA (% by mass)*3 | 0.6 | 10.5 | 9.5 | 11.9 | 10.9 | 12.9 |
| Properties | Melting point (° C.) | 32 | 8 | 8 | 7 | 8 | 8 |
|  | Moisture (% by mass) | 0.03 | 1.09 | 2.12 | 3.03 | 0.13 | 0.09 |
|  | Molar ratio (—) *4 | 45.0 | 7.0 | 6.9 | 7.0 | 3.6 | 5.1 |
|  | pH (—) *5 | 7.4 | 4.1 | 4.1 | 4.2 | 4.2 | 3.9 |
|  | Component (A) residual ratio (%) *6 | 83.6 | 65.6 | 57.4 | 47.5 | 47.6 | 55.0 |

TABLE 2-continued

| | Comparative Example 1 | Comparative Example 2 | Comparative Example 3 | Comparative Example 4 | Comparative Example 5 | Comparative Example 6 |
|---|---|---|---|---|---|---|
| Production trouble — Clogging of supply piping | Occurred | Not occurred | Not occurred | Not occurred | Not occurred | Not occurred |
| Clogging of thermal decomposition column | — | Occurred | Occurred | Occurred | Occurred | Occurred |

*1: Component (A): N-(1-methoxyethyl)acetamide
*2Component (B): acetamide
*3N-vinylacetamide
*4: Component (A)/Component (B) (molar ratio)
*5: pH of 5% by mass aqueous solution
*6: Thermal stability evaluation As shown in Table 1, it was ascertained that the compositions in Examples 1 to 10, satisfying all of the conditions (1) to (4) and comprising component (A) and component (B) do not cause a trouble during production and can produce the N-vinylcarboxylic acid amide stably.

In contrast, as shown in Table 2, it was ascertained that the compositions in Comparative Examples 1 to 6, comprising component (A) and component (B), do not satisfy one of the conditions (1) to (4), and therefore a production trouble occurs and it is difficult to produce the N-vinylcarboxylic acid amide stably.

INDUSTRIAL APPLICABILITY

In production of an N-vinylcarboxylic acid amide, use of the composition of the present invention enables avoiding a production trouble, such as solidification of raw material components in supply piping and clogging in a thermal decomposition column, and enables more stable production than conventional use of an N-(1-alkoxyethyl)carboxylic acid amide singly or use of a conventional composition comprising an N-(1-alkoxyethyl)carboxylic acid amide.

The enhancement and improvement of productivity are due to the composition comprising an N-(1-alkoxyethyl)carboxylic acid amide being a precursor for the N-vinylcarboxylic acid amide, therefore enabling more stable production without introducing expensive temperature control facilities or improving a thermal decomposition reactor, and thereby continuous productivity is also improved. In addition, for example, because the range of setting the operable temperature of supply piping can be expanded, and generation of impurities due to slight temperature setting unevenness or the like in a thermal decomposition reactor including a vaporizer is suppressed, the range of usable options for facilities can therefore be expanded more than that in the past. Further, from the same reason, the composition is unlikely to be subjected to an influence of the installation environment for production facilities, such as, for example, ambient temperature that gives an influence on piping temperature or the like, and therefore the composition also has an advantage that barriers in introducing new production facilities are reduced from the viewpoint in terms of cost and regions.

In this way, the N-(1-alkoxyethyl)carboxylic acid amide-containing composition of the present invention enables reducing restrictions in terms of the operating conditions and the options for facilities in addition to realization of more stable productivity than in conventional facilities, therefore further enables lowering a barrier when new production facilities are introduced, and is industrially extremely useful.

The invention claimed is:

1. A method for producing an N-vinylcarboxylic acid amide by a process which inhibits clogging of piping, comprising thermally decomposing or catalytically decomposing a composition for producing an N-vinylcarboxylic acid amide,
wherein the composition comprises:
component (A) which is an N-(1-alkoxyethyl)carboxylic acid amide; and
component (B) which is a carboxylic acid amide other than the N-(1-alkoxyethyl)carboxylic acid amide and the N-vinylcarboxylic acid amide,
wherein a content of the component (A) in a total amount of the composition is 70.0 to 92.0 mass %, and
wherein the composition satisfies the following conditions (1) to (4):
(1) the composition has a melting point of 0 to 20° C.;
(2) a water content is 0 to 1.00% by mass in a total amount of the composition;
(3) a molar ratio of the component (A) to the component (B) is 4.0:1 to 20.0:1; and
(4) when pure water is added to composition to form an aqueous solution having a concentration of the composition of 5% by mass, a pH of the aqueous solution is 4.0 to 8.0.

2. The method for producing an N-vinylcarboxylic acid amide according to claim 1, wherein the component (A) is a compound represented by the following formula (I):

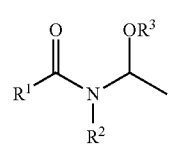

(I)

wherein $R^1$ represents an alkyl group having 1 to 5 carbon atoms, $R^2$ represents a hydrogen atom or an alkyl group having 1 to 5 carbon atoms, and $R^3$ represents an alkyl group having 1 to 5 carbon atoms.

3. The method for producing an N-vinylcarboxylic acid amide according to claim 1, wherein the component (B) is a compound represented by the following formula (II):

(II)

wherein $R^1$ represents an alkyl group having 1 to 5 carbon atoms, and $R^2$ represents a hydrogen atom or an alkyl group having 1 to 5 carbon atoms.

4. The method for producing an N-vinylcarboxylic acid amide according to claim 1, wherein the component (A) is an N-(1-methoxyethyl)carboxylic acid amide.

5. The method for producing an N-vinylcarboxylic acid amide according to claim 1, wherein the component (A) is N-(1-methoxyethyl)acetamide.

6. The method for producing an N-vinylcarboxylic acid amide according to claim 1, wherein the component (B) is acetamide.

7. The method for producing an N-vinylcarboxylic acid amide according to claim 1, wherein when the composition is evaluated by retaining the composition under a condition of 160° C. at normal pressure in the atmosphere for 4 hours and determining a residual ratio (%) of the component (A) in the composition, the residual ratio is 70% or more.

8. The method for producing an N-vinylcarboxylic acid amide according to claim 1, wherein a content of the component (A) in a total amount of the composition is 75.0 to 92.0% by mass.

9. The method for producing an N-vinylcarboxylic acid amide according to claim 1, wherein a total content of the component (A) and the component (B) in a total amount of the composition is 75.0 to 99.0% by mass.

\* \* \* \* \*